United States Patent
Curic-Bawden et al.

(10) Patent No.: US 11,744,259 B2
(45) Date of Patent: Sep. 5, 2023

(54) METHOD OF PRODUCING A FERMENTED MIL K PRODUCT USING LACTOBACILLUS CASEI

(71) Applicant: Chr. Hansen A/S, Hoersholm (DK)

(72) Inventors: Mirjana Curic-Bawden, Brookfield, WI (US); Luciana Luciana Jimenez, Paris (FR); Mette Oehrstroem Runge, Snekkersten (DK); Karen Guillotte, Etréchy (FR); Pia Frost Jensen, Birkeroed (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 16/070,466

(22) PCT Filed: Jan. 23, 2017

(86) PCT No.: PCT/EP2017/051299
§ 371 (c)(1),
(2) Date: Jul. 16, 2018

(87) PCT Pub. No.: WO2017/125600
PCT Pub. Date: Jul. 27, 2017

(65) Prior Publication Data
US 2019/0082707 A1    Mar. 21, 2019

(30) Foreign Application Priority Data
Jan. 21, 2016   (EP) ..................................... 16152207

(51) Int. Cl.
*A23C 9/152*   (2006.01)
*A23C 9/123*   (2006.01)
*C12N 1/20*    (2006.01)
*C12R 1/46*    (2006.01)
*C12R 1/225*   (2006.01)
*C12R 1/245*   (2006.01)

(52) U.S. Cl.
CPC ............ *A23C 9/1238* (2013.01); *A23C 9/152* (2013.01); *C12N 1/205* (2021.05); *A23Y 2220/17* (2013.01); *A23Y 2220/29* (2013.01); *A23Y 2240/75* (2013.01); *C12R 2001/225* (2021.05); *C12R 2001/245* (2021.05); *C12R 2001/46* (2021.05)

(58) Field of Classification Search
CPC ...... A23C 9/1238; A23C 9/152; C12N 1/205; C12R 2001/225; C12R 2001/245; C12R 2001/46; A23Y 2220/17; A23Y 2220/29; A23Y 2240/75
USPC ......................................................... 426/43
See application file for complete search history.

(56) References Cited

U.S. PATENT DOCUMENTS

| | | | |
|---|---|---|---|
| 4,912,047 A | | 3/1990 | Matrozza et al. |
| 5,382,438 A | | 1/1995 | Hottinger et al. |
| 6,033,691 A | * | 3/2000 | Cravero ............... A23C 9/1234 426/43 |
| 6,875,601 B1 | * | 4/2005 | Benbadis ............. A23C 9/1238 424/439 |
| 2005/0196388 A1 | | 9/2005 | Benbadis et al. |
| 2007/0292561 A1 | | 12/2007 | Garault et al. |
| 2009/0238921 A1 | | 9/2009 | Druesne et al. |
| 2011/0064848 A1 | | 3/2011 | Wlaschin et al. |
| 2011/0150852 A1 | | 6/2011 | Chambaud et al. |
| 2011/0206805 A1 | | 8/2011 | Rattray et al. |
| 2013/0149415 A1 | | 6/2013 | Marchal et al. |
| 2013/0295226 A1 | | 11/2013 | Hornbaek et al. |
| 2014/0220177 A1 | | 8/2014 | Druesne et al. |

FOREIGN PATENT DOCUMENTS

| | | | | |
|---|---|---|---|---|
| EP | 2957180 A1 | * | 12/2015 | ........... A23C 9/1238 |
| WO | WO-01/95736 A2 | | 12/2001 | |
| WO | WO-2015/193459 A1 | | 12/2015 | |
| WO | WO-2015193459 A1 | * | 12/2015 | ........... A23C 9/1238 |

OTHER PUBLICATIONS

Aryana, K. J. et al. LwT40: 1808-1814 (2007) (Year: 2007).*
Rajagopal, S. N. et al. J. Dairy Sci., 73: 894-899 (1990) (Year: 1990).*
Zhang, J. Biotechnol Bioprocess Eng. 17: 283-289 (Year: 2012).*
Sidira, M. et al. J. Dairy Sci. 96: 3369-3377 (Year: 2013).*

* cited by examiner

Primary Examiner — Hamid R Badr
(74) Attorney, Agent, or Firm — Foley & Lardner LLP

(57) ABSTRACT

The present invention relates to a method of producing a fermented milk product comprising adding lactic acid bacteria to milk, wherein the bacteria comprise *Lactobacillus casei* and at least one further strain of lactic acid bacteria of a species other than *Lactobacillus casei*, wherein the further strain has a deficiency in lactose metabolism but is capable of metabolizing one or several carbohydrates other than lactose present in the milk.

16 Claims, 3 Drawing Sheets

METHOD OF PRODUCING A FERMENTED MILK PRODUCT USING LACTOBACILLUS CASEI

CROSS-REFERENCE TO RELATED APPLICATIONS

The present application is the U.S. National Stage of International Application PCT/EP2017/051299, filed Jan. 23, 2017, and claims priority to European Patent Application No. 16152207.3, filed Jan. 21, 2016.

FIELD OF THE INVENTION

The present invention relates to a method of producing a fermented milk product comprising adding lactic acid bacteria to milk, wherein the bacteria comprise *Lactobacillus casei* and at least one further strain of lactic acid bacteria of a species other than *Lactobacillus casei*, such as *Streptococcus thermophilus*.

BACKGROUND OF THE INVENTION

Cultured probiotic beverages, also known as probiotic shots, frequently contain *Lactobacillus casei* or *Lactobacillus paracasei*. In the present application the term *L. casei* is used to refer to bacteria of the species *L. casei* or *L. paracasei*. These probiotic beverages are very popular in many parts of the world, including China, Korea and the Far East region as well as Mexico. In further regions in the world the popularity of these beverages also increases.

The product is typically obtained by fermentation of milk using a single strain of *L. casei*. The growth of *L. casei* in milk is slow and as a consequence the fermentation is slow. The fermentation generally requires from 50 to 96 hours As a further consequence of the slow growth, the fermentation often requires specific measures to prevent contamination and cross contamination with other lactic acid bacteria.

The *L. casei* strains are grown until reaching a pH value of 4.2 to 3.7. At that stage the fermented milk is processed and optionally diluted with syrup in a ratio of fermented milk:syrup of between 30:60 and 75:25. The final product is typically packaged in servings of 65-100 ml. The target cell count of *L. casei* in the final diluted fermented milk beverage is higher than $1 \times 10^8$ CFU/ml.

To increase the acidification and thus shorten the production time, *L. casei* has been fermented in combination with other lactic acid bacteria species, including St. *thermophilus* for example using FD-DVS CT-01. With this approach the fermentation time was reduced to about 15 to 20 hours. However, the adjunct species grew faster than *L. casei* and the acid generated due to growth of the adjunct culture caused inhibition of growth of *L. casei*, which reached a concentration of only to 3 to $5 \times 10^7$ CFU/ml. There is thus still a need for improving methods for producing a fermented milk product which methods using *L. casei* for fermentation.

SUMMARY OF THE INVENTION

This problem is now solved by the present invention, which is directed to a method of producing a fermented milk product comprising adding lactic acid bacteria to milk, wherein the bacteria comprise *Lactobacillus casei* and at least one further strain of lactic acid bacteria of a species other than *Lactobacillus casei*, wherein the further strain has a deficiency in lactose metabolism but is capable of metabolizing one or several carbohydrates other than lactose present in the milk.

The present inventors surprisingly found that the problems encountered when generating fermented milk products using *L. casei* can be overcome by fermenting the milk with *L. casei* and at least one further strain with a deficiency in lactose metabolism. The further strain may for example be capable to metabolize sucrose, galactose and/or glucose. One or several of these carbohydrates can be added in low concentration to the milk to be fermented. The further strain will metabolize these carbohydrates quickly and thus begin to acidify the milk quickly. The acidification reduces the risk of growth of undesired lactic acid bacteria due to contamination. The growth of the further strain accelerates the growth of *L. casei*. This is apparently due to the fact that the further strain produces amino acids and peptides in the milk by proteolysis of casein and other milk proteins. The amino acids and peptides accelerate the growth of *L. casei*. However, the further strain will not grow to such an extent or acidify the milk to such an extent that the growth of *L. casei* is significantly inhibited. In the methods of producing a fermented milk product of the present invention *L. casei* achieves the same maximum cell count than in methods of producing *L. casei* without the use of a further LAB. In other words a high concentration of *L. casei* is achieved in a shorter period of time while the risk of contamination is reduced.

In one aspect the at least one further strain of lactic acid bacteria having a deficiency in lactose metabolism is a proteolytic strain. In a preferred aspect, the at least one further strain of lactic acid bacteria having a deficiency in lactose metabolism is a highly proteolytic strain.

In a related aspect the at least one further strain of lactic acid bacteria having a deficiency in lactose metabolism is a bacterium of the species *Streptococcus thermophilus* and/or *Lactobacillus delbrueckii* subsp. *bulgaricus*.

Further embodiments of the invention relate to the use of *L. casei* bacteria and at least one further strain of lactic acid bacteria of a species other than *L. casei*, for producing a fermented milk product, wherein the further strain has a deficiency in lactose metabolism but is capable of metabolizing one or several carbohydrates other than lactose present in the milk.

The present invention also provides compositions comprising bacteria of the species *L. casei* and bacteria of at least one further strain of lactic acid bacteria, wherein the at least one further strain of lactic acid bacteria has a deficiency in lactose metabolism. The at least one further bacterium present in the compositions with a deficiency in lactose metabolism is preferably a bacterium of the species *Streptococcus thermophilus* and/or *Lactobacillus delbrueckii* subsp. *bulgaricus*.

In another embodiment the present invention provides food or feed products comprising bacteria of the species *L. casei* and bacteria of at least one further strain of lactic acid bacteria, wherein the at least one further strain of lactic acid bacteria has a deficiency in lactose metabolism. In particular, the food or feed product can be a fermented milk beverage.

DETAILED DISCLOSURE OF THE INVENTION

In general the present invention provides methods of producing a fermented milk product comprising adding lactic acid bacteria to milk, wherein the bacteria comprise *Lactobacillus casei* and at least one further strain of lactic acid bacteria of a species other than *Lactobacillus casei*, wherein the further strain has a deficiency in lactose metabolism but is capable of metabolizing one or several carbohydrates other than lactose present in the milk.

In the context of the present application, the term "milk" is broadly used in its common meaning to refer to liquids produced by the mammary glands of animals or by plants. In accordance with the present invention the milk may have been processed and the term "milk" includes whole milk, skim milk, fat-free milk, low fat milk, full fat milk, lactose-reduced milk, or concentrated milk. Fat-free milk is non-fat or skim milk product. Low-fat milk is typically defined as milk that contains from about 1% to about 2% fat. Full fat milk often contains 2% fat or more. The term "milk" is intended to encompass milks from different mammals and plant sources. Mammal sources of milk include, but are not limited to cow, sheep, goat, buffalo, camel, llama, mare and deer. Plant sources of milk include, but are not limited to, milk extracted from soy bean, pea, peanut, barley, rice, oat, quinoa, almond, cashew, coconut, hazelnut, hemp, sesame seed and sunflower seed.

In the methods and products of the present invention, milk derived from cows is most preferably used as a starting material for the fermentation.

Lactose-reduced and fat-reduced milk can be used in the methods of the present invention. Lactose-reduced and fat-reduced milk are commercially available and can be produced according to methods well known in the art, including hydrolyzing the lactose by lactase enzyme to glucose and galactose, or by nanofiltration, electrodialysis, ion exchange chromatography and centrifugation.

The term "milk base" is broadly used in the present application to refer to a composition based on milk or milk components which can be used as a medium for growth and fermentation of LAB. The milk base comprises components derived from milk and any other component that can be used for the purpose of growing or fermenting LAB.

As already indicated above, the terms "*Lactobacillus casei*" and "*L. casei*" are used the present application to refer to bacteria of the species *L. casei* or *L. paracasei*. Any strain of *L. casei* can be used in the context of the present invention, including mixtures of strains. Preferably food-grade strains of *L. casei* are used. Respective strains are available from numerous sources.

In the context of the present application, the term "lactic acid bacteria" or "LAB" is used to refer to food-grade bacteria producing lactic acid as the major metabolic end-product of carbohydrate fermentation. These bacteria are related by their common metabolic and physiological characteristics and are usually Gram positive, low-GC, acid tolerant, non-sporulating, non-respiring, rod-shaped bacilli or cocci. During the fermentation stage, the consumption of lactose by these bacteria causes the formation of lactic acid, reducing the pH and leading to the formation of a protein coagulum. These bacteria are thus responsible for the acidification of milk and for the texture of the dairy product. As used herein, the term "lactic acid bacteria" encompasses, but is not limited to, bacteria belonging to the genus of *Lactobacillus* spp., *Bifidobacterium* spp., *Streptococcus* spp., *Lactococcus* spp., such as *Lactobacillus delbrueckii* subsp. *bulgaricus, Streptococcus thermophilus, Lactobacillus lactis, Bifidobacterium animalis, Lactococcus lactis, Lactobacillus paracasei, Lactobacillus plantarum, Lactobacillus helveticus, Lactobacillus acidophilus, Bifidobacterium breve* and *Leuconostoc* spp.

The fermentation step of the process for manufacturing fermented dairy products comprises the addition of lactic acid bacteria to milk. The bacteria added to the milk are often identified as a starter culture. The term "starter culture" as used in the present context refers to a culture of one or more food-grade microorganisms, in particular lactic acid bacteria, which are responsible for the acidification of the milk base. Starter cultures may be fresh, frozen or freeze-dried. For the production of a fermented dairy product, the starter can be added in any amount. Typically, the starter is added in an amount to achieve a concentration from 0.001 to 3%, preferably from 0.001 to 0.025% by volume of the total amount of milk.

The terms "deficiency in lactose metabolism" and "lactose deficient" are used in the context of the present invention to characterize LAB which either partially or completely lost the ability to use lactose as a source for cell growth or maintaining cell viability. Respective LAB are capable of metabolizing one or several carbohydrates selected from the group consisting of sucrose, galactose and glucose, or another fermentable carbohydrate. Since these carbohydrates are not naturally present in milk in sufficient amounts to support fermentation by lactose deficient mutants, it will be necessary to add these carbohydrates to the milk. Lactose deficient and partially deficient LAB can be characterized as white colonies on a medium containing lactose and X-Gal.

In one aspect the present invention therefore provides a method of producing a fermented milk product comprising adding lactic acid bacteria to milk, wherein the bacteria comprise *Lactobacillus casei* and at least one further strain of lactic acid bacteria of a species other than *Lactobacillus casei*, wherein the at least one further strain of lactic acid bacteria having a deficiency in lactose metabolism is capable of metabolizing one or more carbohydrates selected from the group consisting of sucrose, galactose and glucose, and wherein the said carbohydrate is added to the milk before fermentation.

In a preferred embodiment, a method of producing a fermented milk product is provided, wherein the strain with a deficiency in lactose metabolism is a proteolytic strain, for example a proteolytic strain of *S. thermophilus*, more preferably the further strain with a deficiency in lactose metabolism is *S. thermophilus* DSM 28952.

As indicated above, the growth of the further strain accelerates the growth of *L. casei*, which is apparently due to the fact that the further strain provides amino acids and peptides in the milk by proteolysis of casein and other milk proteins. Consequently, the use of a further LAB with proteolytic activity represents an advantageous embodiment of the present invention.

In accordance with the present invention, a LAB is a proteolytic LAB if it contains an active cell wall proteinase. A cell wall proteinase hydrolyzes milk proteins, such as casein, and thus improves the quality of milk as a medium for rapid growth of LAB having amino acid auxotrophies. Cell wall proteinases have been identified and characterized in detail in numerous LAB, including the PrtP of *L. lactis*, the PrtS of *S. thermophilus* and the PrtB of *Lb. bulgaricus*. Proteolytic LAB can thus be identified by the presence of the gene encoding the cell wall proteinase.

Additionally, proteolytic LAB can be identified by the fluorescent substrate fluorescein isothiocyanate labeled casein or FITC casein assay, wherein an increase in fluorescence caused by the growth of the strain for 6 hours in a medium containing fluorescently labeled casein in comparison to control samples without cells of the strain is determined. Full details of the assay are provided in Example 1.

Accordingly, the present invention provides methods of producing a fermented milk product comprising adding lactic acid bacteria to milk, wherein the bacteria comprise *Lactobacillus casei* and at least one further strain of lactic acid bacteria of a species other than *Lactobacillus casei*, wherein the further strain has a deficiency in lactose metabolism but is capable of metabolizing one or several carbohydrates other than lactose present in the milk and wherein the further strain with a deficiency in lactose metabolism is a proteolytic strain of *S. thermophilus,* wherein a proteolytic strain is characterized by:
  (a) the presence of an active cell wall proteinase; and/or
  (b) an increase in fluorescence caused by the growth of the strain for 6 hours in a medium containing fluorescently labeled casein in comparison to control samples.

In a particular embodiment of the method of the invention, the further strain with a deficiency in lactose metabolism is a proteolytic strain of *S. thermophilus*, wherein a proteolytic strain is characterized by:
  (a) the presence of an active cell wall proteinase; and/or
  (b) an increase in fluorescence caused by the growth of the strain for 6 hours in a medium containing fluorescently labeled casein in comparison to control samples.

In a particular embodiment of the method of the invention, the proteolytic *S. thermophilus* strain is selected form the group consisting of:
  (a) a *Streptococcus thermophilus* strain, which strain is:
    (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28952;
    (ii) or a strain derived from DSM 28952, wherein the derived strain is further characterized as having the ability to generate white colonies on a medium containing lactose and X-Gal;
  (b) a *Streptococcus thermophilus* strain, which strain is:
    (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28953;
    (ii) or a strain derived from DSM 28953, wherein the derived strain is further characterized as having the ability to generate white colonies on a medium containing lactose and X-Gal;

In a particular embodiment of the method of the invention, the *Lactobacillus casei* strain is selected from the group consisting of *L. casei*, CRL 431 deposited as ATCC 55544 and *L. casei*, CHCC2115 deposited as DSM19465.

In a further aspect the method of the present invention use lactic acid bacteria selected from one or more of the following strains:
  (a) *L. casei*, CRL 431 deposited as ATCC 55544;
  (b) *L. casei*, CHCC2115 deposited as DSM19465;
  (c) *S. thermophilus*, CHCC17861 deposited as DSM28952, a strain with a deficiency in lactose metabolism.

In a preferred aspect the methods use lactic acid bacteria selected from one of the following combination of strains:
  (i) *L. casei*, CRL 431 deposited as ATCC 55544, and *S. thermophilus*, CHCC17861
  (ii) *L. casei*, CHCC2115 deposited as DSM19465 with DSMZ-Deutsche Sammlung von Mikroorganismen und Zellkulturen GmbH, Inhoffenstr. 7B, D-38124 Braunschweig, on 2007 Jun. 27, and *S. thermophilus*, CHCC17861 deposited as DSM 28952, a strain with a deficiency in lactose metabolism.

Lactose deficient LAB and methods of producing the same have been generally described, exemplified and deposited in prior Patent applications, including WO 2013/160413, PCT/EP2015/063767 and PCT/EP2015/063742, which describe methods for producing LAB with a deficiency in lactose metabolism and specific strains obtained by these methods.

Any LAB with a deficiency in lactose metabolism and mixtures of different strains can be used in the method of the present invention. In a preferred embodiment of the method of the invention, the further strain with lactose deficiency is selected from the group consisting of *Streptococcus thermophilus* (ST) and *Lactobacillus delbrueckii* ssp. *bulgaricus* (LB). These lactose deficient LAB metabolize a carbohydrate other than lactose, for example sucrose. In a preferred embodiment of the method of the invention, the further strain is selected from the group consisting of:
  (a) a *Streptococcus thermophilus* strain, which strain is:
    (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28952;
    (ii) or a strain derived from DSM 28952, wherein the derived strain is further characterized as having the ability to generate white colonies on a medium containing lactose and X-Gal;
  (b) a *Streptococcus thermophilus* strain, which strain is:
    (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28953;
    (ii) or a strain derived from DSM 28953, wherein the derived strain is further characterized as having the ability to generate white colonies on a medium containing lactose and X-Gal;
  (c) a *Lactobacillus delbrueckii* ssp. *bulgaricus* strain, which strain is:
    (i) the strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28910;
    (ii) or a strain derived from DSM 28910, wherein the derived strain is further characterized as having the ability to generate white colonies on a medium containing lactose and X-Gal.

The term "capable of metabolizing one or several carbohydrates other than lactose present in the milk" is used in the context of the present invention to describe the metabolic activity of lactose deficient LAB which causes production of lactic acid as the major metabolic end-product of carbohydrate fermentation using a carbohydrate other than lactose. To achieve detectable metabolic activity on the basis of a carbohydrate other than lactose the other carbohydrates may have to be added to the milk.

In certain embodiments, the methods of the present invention use LAB capable to metabolize sucrose, galactose and/or glucose. The invention therefore provides methods, wherein sucrose, galactose and/or glucose are added to the milk before fermentation. The amount of carbohydrates to be added to the milk can be easily determined on the basis of the LAB used and the desired acidification primarily caused by the LAB other than *L. casei*. In most instances sucrose, galactose and/or glucose are added to the milk in an amount resulting in a concentration in the range of 0.4 g/l to 10 g/l, or in the range of 1 g/l to 8 g/l or in the range of 2 g/l to 6 g/l.

The ratio of bacterial cell count of *L. casei* and at the least one further strain of LAB with a deficiency in lactose metabolism in the starter culture or the milk at the beginning of fermentation can be easily determined by one of ordinary skill. In a particular embodiment the ratio is in the range of *L. casei*: further strain of LAB of 95:5 to 5:95. A preferred ratio is in the range of 80:20 to 20:80, preferably 70:30 to 30:70, more preferably 60:40 to 40:60, such as about 50:50.

In one embodiment of the methods of the present invention the fermentation is carried out at a temperature between 22 and 45° C., preferably around 30° C. Fermentation is commonly carried out until a pH of below 4.5 is reached, preferably a pH of around 4.0, such as a pH between 3.7 and 4.3.

The methods of the present invention are in particular characterized by achieving high concentrations of *L. casei*, preferably a concentration of $1 \times 10^8$ to $5 \times 10^9$ CFU/g, more preferably $1 \times 10^9$ to $5 \times 10^9$ CFU/g, and most $1 \times 10^9$ to $3 \times 10^9$ CFU/g. These concentrations are achieved in a relatively short period of time, for example in a period of between 30 and 50 hours, most preferably in a period of between 35 and 45 hours.

The present invention in particular provides methods of producing a fermented milk product comprising adding lactic acid bacteria to milk, wherein the bacteria comprise:
(a) *L. casei* and
(b) a bacterium with a deficiency in lactose metabolism selected from the *Streptococcus thermophilus, Lactobacillus delbrueckii* ssp. *bulgaricus* and mixtures thereof,
wherein the bacteria are added to the milk in a ratio of (a):(b) of 95:5 to 5:95, and wherein the method produces a concentration of *L. casei* of $1 \times 10^8$ to $1 \times 10^{11}$ CFU/g in a period of 35 and 45 hours.

The present invention further provides methods of producing a fermented milk product comprising adding lactic acid bacteria to milk, wherein the bacteria comprise:
(a) a strain of *L. casei* strain selected from
   (i) *L. casei*, CRL 431 deposited as ATCC 55544; and/or
   (ii) *L. casei*, CHCC2115 deposited as DSM19465;
(b) a bacterium with a deficiency in lactose metabolism selected from the *Streptococcus thermophilus, Lactobacillus delbrueckii* ssp. *bulgaricus* and mixtures thereof, preferably comprising the strain *S. thermophilus*, CHCC17861 deposited as DSM 28952;
wherein the bacteria are added to the milk in a ratio of (a):(b) of 95:5 to 5:95, and wherein the method produces a concentration of *L. casei* of $1 \times 10^8$ to $1 \times 10^{11}$ CFU/g in a period of 35 and 45 hours.

In a preferred embodiment the at least one further strain of lactic acid bacteria with a deficiency in lactose metabolism is a bacterium of the species selected from the group consisting of *Streptococcus thermophilus* and *Lactobacillus delbrueckii* subsp. *bulgaricus*.

In a particular embodiment of the method of the invention, the at least one further strain of lactic acid bacteria having a deficiency in lactose metabolism is a bacterium of the species *Streptococcus thermophilus*.

In a particular embodiment of the method of the invention, the at least one further strain of lactic acid bacteria having a deficiency in lactose metabolism is a bacterium of the species *Lactobacillus delbrueckii* subsp. *bulgaricus*.

In a related embodiment the present invention provides the use of *L. casei* bacteria and at least one further strain of lactic acid bacteria of a species other than *L. casei*, for producing a fermented milk product, wherein the further strain has a deficiency in lactose metabolism but is capable of metabolizing one or several carbohydrates other than lactose present in the milk. This use of *L. casei* bacteria and of the at least one further strain of lactic acid bacteria may comprise the addition of sucrose, galactose and/or glucose to the milk.

In preferred embodiments the use is also characterized in that the at least one further strain of lactic acid bacteria with a deficiency in lactose metabolism is a bacterium of the species selected from the group consisting of *Streptococcus thermophilus* and *Lactobacillus* delbrueckii subsp. *bulgaricus*.

In a separate aspect the present invention provides compositions comprising bacteria of the species *L. casei* and bacteria of at least one further strain of lactic acid bacteria, wherein the at least one further strain of lactic acid bacteria has a deficiency in lactose metabolism. In a particular embodiment of the invention, the composition comprises bacteria of the species *Lactobacillus casei* and bacteria of at least one further strain of lactic acid bacteria according to claim 10, wherein the at least one further bacterium is a bacterium of the species selected from the group consisting of *Streptococcus thermophilus* and *Lactobacillus delbrueckii* subsp. *bulgaricus*.

The composition of the present invention may comprise any number of further components, including fermented milk, food additives, stabilizers, cryoprotective agents, flavoring agents, artificial sweeteners and the like. The composition may be used as a starter culture for the production of fermented milk products using the methods of the present invention as described above.

Alternatively, these compositions represent the fermented milk products as such.

The present invention further relates to a food or feed product comprising bacteria of the species *L. casei* and bacteria of at least one further strain of lactic acid bacteria, wherein the at least one further strain of lactic acid bacteria has a deficiency in lactose metabolism.

In a particular embodiment of the food or feed product of the invention, the at least one further strain of lactic acid bacteria is a bacterium of the species selected from the group consisting of *Streptococcus thermophilus* and *Lactobacillus delbrueckii* subsp. *bulgaricus*.

A particular embodiment of the food or feed product of the invention comprises *L. casei* in a concentration of $1 \times 10^8$ CFU/g to $5 \times 10^9$ CFU/g, preferably $1 \times 10^9$ CFU/g to $5 \times 10^9$ CFU/g, and more preferably $1 \times 10^9$ CFU/g to $3 \times 10^9$ CFU/g.

In a particular embodiment of the food or feed product of the invention, the food or feed product is a fermented milk beverage.

In particularly preferred embodiments the food or feed products comprise:
(a) *L. casei* in a concentration of *L. casei* of $1 \times 10^8$ to $1 \times 10^{11}$ CFU/g or in a concentration of $1 \times 10^9$ to $1 \times 10^{11}$ CFU/g and
(b) a bacterium with a deficiency in lactose metabolism selected from the *Streptococcus thermophilus, Lactobacillus delbrueckii* ssp. *bulgaricus* and mixtures thereof.

The present invention for example provides food or feed products comprising:
(a) a strain of *L. casei* in a concentration of *L. casei* of $1 \times 10^8$ to $1 \times 10^{11}$ CFU/g or in a concentration of $1 \times 10^9$ to $1 \times 10^{11}$ CFU/g, wherein the strain is selected from:
   (i) *L. casei*, CRL 431 deposited as ATCC 55544; and/or
   (ii) *L. casei*, CHCC2115 deposited as DSM19465; and
(b) a bacterium with a deficiency in lactose metabolism selected from the *Streptococcus thermophilus, Lacto-* bacillus delbrueckii ssp. bulgaricus and mixtures thereof, preferably comprising S. thermophilus, CHCC17861.

Any food or feed product can be any fermented milk product, including yoghurt, fruit yoghurt, yoghurt beverage or cheese.

In the context of the present application, the term "yoghurt" refers to products comprising *Streptococcus thermophilus* and *Lactobacillus delbrueckii* subsp. *bulgaricus* and optionally other microorganisms such as *Lactobacillus delbrueckii* subsp. *lactis*, *Bifidobacterium animalis* subsp. *lactis*, *Lactococcus lactis*, *Lactobacillus acidophilus* and *Lactobacillus paracasei*, or any microorganism derived therefrom. The lactic acid strains other than *Streptococcus thermophilus* and *Lactobacillus delbrueckii* subsp. *bulgaricus*, are included to give the finished product various properties, such as the property of promoting the equilibrium of the flora. As used herein, the term "yoghurt" encompasses set yoghurt, stirred yoghurt, drinking yoghurt, Petit Suisse, heat treated yoghurt, strained or Greek style yoghurt characterized by a high protein level and yoghurt-like products.

In particular, term "yoghurt" encompasses, but is not limited to, yoghurt as defined according to French and European regulations, e.g. coagulated dairy products obtained by lactic acid fermentation by means of specific thermophilic lactic acid bacteria only (i.e. *Lactobacillus delbrueckii* subsp. *bulgaricus* and *Streptococcus thermophilus*) which are cultured simultaneously and are found to be live in the final product in an amount of at least 10 million CFU (colony-forming unit)/g. Yoghurts may optionally contain added dairy raw materials (e.g. cream) or other ingredients such as sugar or sweetening agents, one or more flavoring(s), fruit, cereals, or nutritional substances, especially vitamins, minerals and fibers, as well as stabilizers and thickeners. In one alternative, the yoghurt meets the specifications for fermented milks and yoghurts of the AFNOR NF 04-600 standard and/or the codex StanA-IIa-1975 standard. In order to satisfy the AFNOR NF 04-600 standard, the product must not have been heated after fermentation and the dairy raw materials must represent a minimum of 70% (m/m) of the finished product.

The food products of the present invention also comprise cheese, including Mozzarella, Pizza and Feta cheese produced by applying the methods described above to the technology of cheesemaking well known in the art (Hoier et al. (2010) in The Technology of Cheesemaking, $2^{nd}$ Ed. Blackwell Publishing, Oxford; 166-192).

In a preferred embodiment the present invention provides a fermented milk beverage, such as a fermented yoghurt, obtained by the methods described above. A fermented milk beverage may for example be characterized as comprising:
(a) *L. casei* in a concentration of *L. casei* of $1 \times 10^8$ to $1 \times 10^{11}$ CFU/g or in a concentration of $1 \times 10^9$ to $1 \times 10^{11}$ CFU/g and
(b) a bacterium with a deficiency in lactose metabolism selected from the *Streptococcus thermophilus, Lactobacillus delbrueckii* ssp. *bulgaricus* and mixtures thereof.

This fermented milk beverage may in particular comprise:
(a) a strain of *L. casei* in a concentration of *L. casei* of $1 \times 10^8$ to $1 \times 10^{11}$ CFU/g or in a concentration of $1 \times 10^9$ to $1 \times 10^{11}$ CFU/g, wherein the strain is selected from:
(i) *L. casei*, CRL 431 deposited as ATCC 55544; and/or
(ii) *L. casei*, CHCC2115 deposited as DSM 19465; and
(b) a bacterium with a deficiency in lactose metabolism selected from the *Streptococcus thermophilus, Lacto-*

*bacillus delbrueckii* ssp. *bulgaricus* and mixtures thereof, preferably comprising *S. thermophilus*, CHCC17861.

EXAMPLE 1

FITC Assay: Protocol for measuring Proteinase activity in lactic acid bacteria (LAB), employing Hamilton liquid handling unit.

The cell-wall associated proteinase(s) contribute to rapid growth of LAB in milk. The proteinases are also responsible for the first step in degradation of casein and thereby development of flavor. The assay is based on the fluorescent substrate fluorescein isothiocyanate labeled casein (FITC).

Materials

Costar Deep well plate—2.0 ml
Microtiter plates: Nunc, black plates, (Cat. No. 237105), Nunc (product no. 167008),
MJR PCR plate (V-shaped, product no. HSP-9665)
Hamilton liquid handling robot
Hamilton disposable sterile tips
Calcium chloride dihydrate (Merck Cat. No. 1.02382.1000)
MES hydrate, minimum 99.5% titration (Sigma M8250-1 kg)
Tris, (Sigma Cat. No. 11503)
Samples in Costar deep well plate (2.0 ml)
Enspire, 2300 multilabel reader, PerkinElmer
Control strains: LH-Emfour, batch no. 2995517, material no. 501638
LH-32 batch no. 2990465, material no. 616703 added as thawed DVS (50 µl) to grow up o/n. When using a new batch of control compare proteolytic activity to old batch before using.
500 mM Tris-HCL, pH 8.5:
60.55 g Tris-HCl. Add Milli-Q water to 800 ml, adjust pH to 8.5 with 1M HCl.
Fill with Milli-Q water to 1000 ml.
FITC, FITC-labeled casein (Sigma C3777)
5 mg/ml FITC, prepared in sterile filtered Milli-Q water.
MES 100 mM+ $CaCl_2$), pH 6.5
19.52 g MES and 7.35 g $CaCl_2$). Add water to 800 ml, adjust pH to 6.5, fill water to 1000 ml, sterile filter.
5% TCA
5 g Trichloric acetic acid is dissolved in Milli-Q water to a total volume of 100 ml.
Cultivation medium: BD5-3-broth
Methods
Wash cells
The strains are grown overnight in the appropriate dilution, a 10% inoculation from WS-Plate in deep well plate with 1800 µl BD5-3 broth. *Lactococcus* sp. are incubated at 30° C.; *Lactobacillus* sp. and *Streptococcus* sp. are incubated at 37° C. Wash 3× with cold MES buffer pH 6.5 (centrifuge deep well plate after each wash, 4000 rpm for 4 min at 10° C.), measure OD620, and from there take samples for proteinase activity on FITC substrate and incubate the plate at 37° C. for 6 h.

FITC protocol
  Dispense 8 µl of FITC solution to a MJR PCR microtiter plate (V-shaped wells in order to minimize evaporation during incubation).
  Dispense 40 µl of washed cell suspension to the MJR PCR microtiter plate & seal the plates.
  Incubate MJR PCR microtiter plate for 0-6 h at 37° C. (Lb's & St's).
  Dispense 115 µl of 5% w/v TCA to MJR PCR microtiter plate.
  Incubate the MRJ PCR microtiter plate for 1 h at room temperature or 30 min on ice bath.
  Centrifuge the MJR PCR microtiter plate (3700 rpm for 10 min, 10° C.).
  Dispense 125 µl of Tris-HCl 0.5 M (pH 8.5) to the Nunc Black microtiter plate.
  Aspirate 45 µl from MJR PCR microtiter plate to Nunc Black microtiter plate.
  Read the fluorescence at Exitation 497 nm—Emission 515 nm, on Enspire, 2300 multilabel reader, PerkinElmer.
  T0 Samples without incubation
  T6 Samples were incubated for 6 h at 37° C., immediately after wash with MES-buffer.
  Data treatment: Subtract T0 from T6, make graphs, then divide by OD of the washed cells, make new graphs. Check whether very high activity is due to a low OD. Check whether controls are in normal range.

EXAMPLE 2

Figure 1:
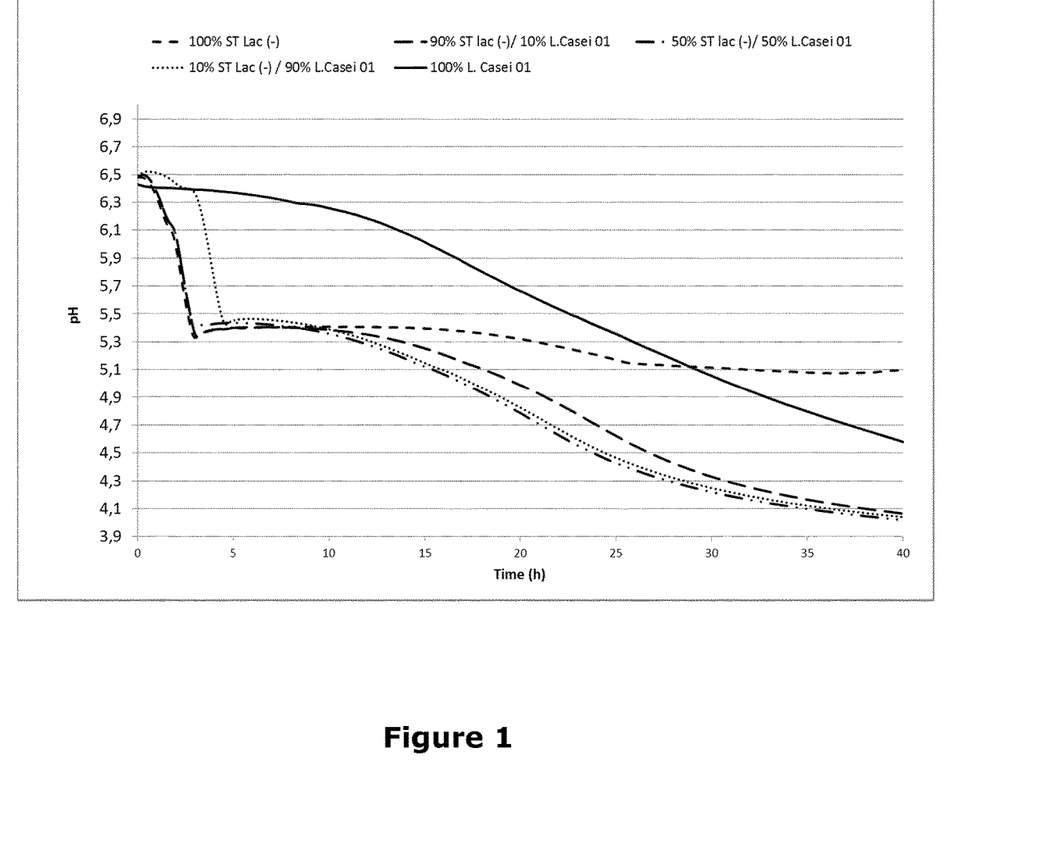
FIG. 1 shows acidification curves of milk using different starter cultures.
Figure 2:
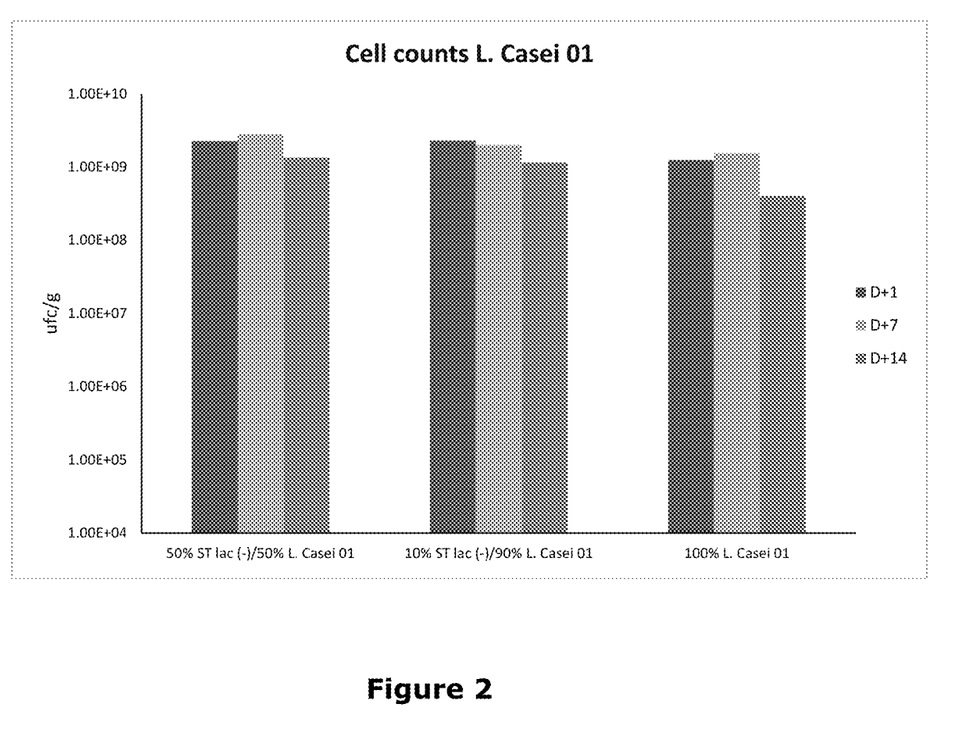
FIG. 2 shows cell counts (CFU/g) of *L. casei* after fermentation and storage.

Milk was fermented using one of the following two different *L. casei* strains of Chr. Hansen alone or in combination with the following *Streptococcus thermophilus* strain of Chr. Hansen:
  *L. casei* CRL 431 deposited as ATCC 55544;
  *L. casei* 01, CHCC2115 deposited as DSM19465; and
  *S. thermophilus*, CHCC17861 deposited as *S. thermophilus* DSM 28952.
  The *S. thermophilus* strain has a deficiency in lactose metabolism.
  When used in combination the following ratios were used:
  (1) 50:50
  (2) 90:90; and
  (3) 10:90.
  *S. thermophilus* with a deficiency in lactose metabolism alone and each of the two *L. casei* strains alone were used as controls.
  Standard milk was used for the trials (3.8% protein, 1.5% fat). Sucrose (0.4% w/v) was added to the milk to allow fast acidification of the *S. thermophilus* with a deficiency in lactose metabolism to pH 5.50. Acidification was performed at 39° C. and at 37° C.
  Development of pH was determined during fermentation. Development of cell count was determined on days 1, 7 and 14 after fermentation.
  Three repetitions were performed to confirm the data.
  Typical results are illustrated in FIGS. 1 and 2. As shown in FIG. 1, *L. casei* 01 alone has a very long lag phase and reaches pH 4.5 only after 40 h of fermentation. However, when combined with *S. thermophilus* with a deficiency in lactose metabolism in different ratios the lag phase is significantly reduced (8 h for *L. casei* 01 alone to achieve pH 6.3; whereas only 1 h when combined with *S. thermophilus* with a deficiency in lactose metabolism). *S. thermophilus* with a deficiency in lactose metabolism alone reduced the pH value to a final pH of 5.1 after sucrose depletion. However, when combined with *L. casei* 01, the acidification continues due to the presence of *L. casei* 01, which is capable to use the lactose present in the milk.
  The same results were obtained using *L. casei* CRL 431 and in trials performed at 37° C. (data not shown).
  *L. casei* 01 cell counts are shown in FIG. 2. FIG. 2 shows that the co-culture of *L. casei* 01 and *S. thermophilus* with a deficiency in lactose metabolism does not reduce the *L. casei* cell counts, in comparison to single strain fermentation.
  As a consequence, the combination of *L. casei* 01 with a Lac (−) ST boosts the *L. casei* 01 without disturbing its growth (no competition). The combination allows a high reduction of the lag phase while maintaining high cell counts.

EXAMPLE 3

Figure 3:
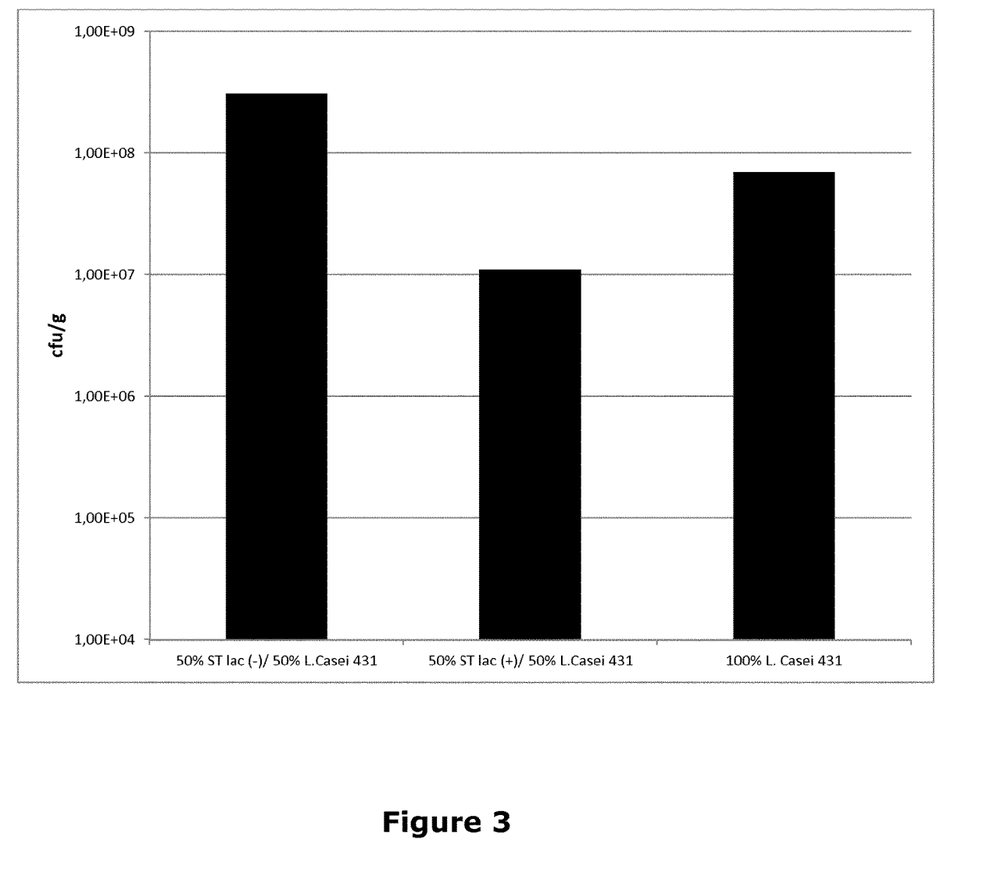
FIG. 3 shows cell counts (CFU/g) of *L. casei* after fermentation and storage.

Milk was fermented using the following *L. casei* strain of Chr. Hansen alone or in combination with the following *Streptococcus thermophilus* strains of Chr. Hansen:
  *L. casei* CRL 431 deposited as ATCC 55544; in combination with
1) *S. thermophilus*, CHCC17861 deposited as *S. thermophilus* DSM 28952. The strain has a deficiency in lactose metabolism (Lac(−)); or
2) *S. thermophilus*, CHCC11977 deposited as DSM22935, with no deficiency in lactose metabolism (mother strain of CHCC17861) (Lac(+)).
  When used in combination the following ratio was used:
  (1) 50:50
  The milk base used for the present experiment is Skimmed Milk Powder (SMP) reconstituted at 9.6%. The milk base was subjected to heat treatment at 99° C. for 15 minutes. Sucrose (0.3% w/v) was added to the milk to allow fast acidification of the *S. thermophilus* with a deficiency in lactose metabolism to pH 5.50. Acidification was performed at 39° C.
  Development of cell count was determined 40 hours after fermentation.
  One repetition of the experiment was performed.
  As will appear from FIG. 3 the *L. casei* cell count was significantly reduced, when the *L. casei* strain was grown together with a conventional *S. thermophilus* strain (no deficiency in lactose metabolism (Lac(+)) as compared to when the *L. casei* is grown alone. Also, the *L. casei* cell count was significantly increased, when the *L. casei* strain was grown together with a *S. thermophilus* strain with a deficiency in lactose metabolism (Lac(−)) as compared to when the *L. casei* is grown alone.

Deposits and Expert Solution

The Applicant requests that a sample of the deposited microorganism should be made available only to an expert approved by the Applicant.
  *Streptococcus thermophilus* strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28952.
  *Streptococcus thermophilus* strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM 28953.
  *Streptococcus thermophilus* strain deposited with DSMZ-Deutsche Sammlung von Mikroorganismen und Zellkulturen GmbH, Inhoffenstr. 7B, D-38124 Braunschweig, on 2009 Sep. 8 under the accession no. DSM22935.

*Lactobacillus delbrueckii* subsp. *bulgaricus* strain deposited with DSMZ-Deutsche Sammlung von Mikroorganismen und Zellkulturen GmbH, Inhoffenstr. 7B, D-38124 Braunschweig, on 2014 Jun. 12 under the accession no. DSM28910.

*Lactobacillus casei* strain deposited with DSMZ-Deutsche Sammlung von Mikroorganismen und Zellkulturen GmbH, Inhoffenstr. 7B, D-38124 Braunschweig, on 2007 Jun. 27 under the accession no. DSM19465.

The deposits were made according to the Budapest treaty on the international recognition of the deposit of microorganisms for the purposes of patent procedure.

The invention claimed is:

1. A method of producing a fermented milk product comprising *Lactobacillus casei*, comprising:
   adding sucrose to milk;
   adding lactic acid bacteria to the milk, wherein the lactic acid bacteria comprise *Lactobacillus casei* and at least one further strain of lactic acid bacteria of a species other than *Lactobacillus casei*, wherein the at least one further strain has a deficiency in lactose metabolism but is capable of metabolizing sucrose, and fermenting the milk with the bacteria.

2. The method of claim 1, wherein the at least one further strain of lactic acid bacteria is capable of metabolizing one or more additional carbohydrates selected from galactose and glucose, and wherein the method further comprises adding said one or more additional carbohydrates to the milk before the fermenting.

3. The method of claim 1, wherein the bacteria comprise *Lactobacillus casei* selected from the group consisting of *L. casei* strain CRL 431 deposited as ATCC 55544 and *L. casei* strain CHCC2115 deposited as DSM19465.

4. The method of claim 1, wherein the at least one further strain is selected from one or more of:
   (a) a *Streptococcus thermophilus* strain deposited at Deutsche Sammlung von Mikroorganismen and Zellkulturen GmbH (DSMZ) under Accession No. DSM 28952;
   (b) a *Streptococcus thermophilus* strain deposited at DSMZ under Accession No. DSM 28953; and
   (c) a *Lactobacillus delbrueckii* ssp. *bulgaricus* strain deposited at DSMZ under Accession No. DSM 28910.

5. The method according to claim 1, wherein the at least one further strain comprises a proteolytic strain of *S. thermophilus*, wherein the proteolytic strain exhibits one or both of (a) the presence of an active cell wall proteinase and (b) an increase in fluorescence caused by growth of the strain for 6 hours in a medium containing fluorescently labeled casein as compared to fluorescence of control samples of control strains.

6. The method of claim 1, wherein the method produces *L. casei* at a concentration of from $1 \times 10^8$ to $5 \times 10^9$ CFU/g.

7. The method of claim 1, wherein the method produces *L. casei* at a concentration of from $1 \times 10^9$ to $5 \times 10^9$ CFU/g.

8. The method of claim 1, wherein the method produces *L. casei* at a concentration of from $1 \times 10^9$ to $3 \times 10^9$ CFU/g.

9. The method according to claim 1, wherein the method results in a shorter acidification time than a comparable method that does not comprise adding the at least one further strain of lactic acid bacteria, and results in higher cell count of *Lactobacillus casei* than a comparable method that comprises adding at least one further strain of lactic acid bacteria that does not have a deficiency in lactose metabolism.

10. A probiotic composition comprising bacteria of the species *L. casei* and bacteria of at least one further strain of lactic acid bacteria, wherein the at least one further strain of lactic acid bacteria has a deficiency in lactose metabolism and is capable of metabolizing sucrose, wherein the composition comprises *L. casei* in an amount from $1 \times 10^8$ CFU/g to $5 \times 10^9$ CFU/g.

11. The composition of claim 10, wherein the at least one further strain of lactic acid bacteria is of a species selected from *Streptococcus thermophilus* and *Lactobacillus delbrueckii* subsp. *bulgaricus*.

12. A probiotic food or feed product comprising bacteria of the species *L. casei* and bacteria of at least one further strain of lactic acid bacteria, wherein the at least one further strain of lactic acid bacteria has a deficiency in lactose metabolism and is capable of metabolizing sucrose, wherein the food or feed product comprises *L. casei* in an amount from $1 \times 10^8$ CFU/g to $5 \times 10^9$ CFU/g.

13. The food or feed product of claim 12, wherein the at least one further strain of lactic acid bacteria is of a species selected from *Streptococcus thermophilus* and *Lactobacillus delbrueckii* subsp. *bulgaricus*.

14. The food or feed product of claim 12, comprising *L. casei* in an amount from $1 \times 10^9$ CFU/g to $5 \times 10^9$ CFU/g.

15. The food or feed product of claim 12, comprising *L. casei* in an amount from $1 \times 10^9$ CFU/g to $3 \times 10^9$ CFU/g.

16. The food or feed product according to claim 12, wherein the food or feed product is a fermented milk beverage.

* * * * *